United States Patent

Bernáth et al.

[11] Patent Number: 4,677,109
[45] Date of Patent: Jun. 30, 1987

[54] 1-(6-(2'-SUBSTIUTED-5', 6', 7', 8'-TETRAHYDRO-4',-OXO-QUINAZOLINO))-3-4-DIHYDRO-6,7-DISUBSTITUTED-ISOQUINOLINE DERIVATIVES AND PHARMACEUTICAL COMPOSTIONS CONTAINING THEM

[75] Inventors: Gábor Bernáth; Jenó Kóbor; János Lázár; Gábor Motika, all of Szeged; Elemer Ezer, Budapest; György Hajós, Budapest; Éva Pálosi, Budapest; Laszlo Denes, Budapest; László Szporny, Budapest, all of Hungary

[73] Assignee: Richter Gedeon Vegyeszeti Syar R.T., Hungary

[21] Appl. No.: 721,807

[22] Filed: Apr. 10, 1985

[30] Foreign Application Priority Data

Apr. 11, 1984 [HU] Hungary .................. 2251-1394/84

[51] Int. Cl.⁴ ................ A61K 31/505; C07D 401/04
[52] U.S. Cl. .................... 514/259; 514/234; 544/116; 544/284; 544/287; 544/289; 546/147
[58] Field of Search .............. 544/284, 287, 289, 116; 514/259, 234

[56] References Cited

U.S. PATENT DOCUMENTS 4,522,945 6/1985 Vandenberk et al. .............. 544/284

OTHER PUBLICATIONS

Bernath, et al., "Acta. Chim. Acad. Sci. Hung.", vol. 65, 1970, pp. 347-368.
Kerley, et al., "J. Pharm. Exp. Ther." vol. 132, 1961, pp. 360-365.
Brown, *Fused Pyrimidines*, Part 1, Quinazolines, 1967, Interscience Publishers, N.Y., pp. 116-120, 133-134.

Primary Examiner—Glennon H. Hollrah
Assistant Examiner—James H. Turnipseed
Attorney, Agent, or Firm—Keil & Weinkauf

[57] ABSTRACT

The invention relates to new 1-[6-(2'-substituted-5', 6', 7', 8'-tetrahydro-4'-oxo-quinazolino)]-3,4-dihydro-6,7-disubstituted-isoquinoline derivatives of the formula (I)

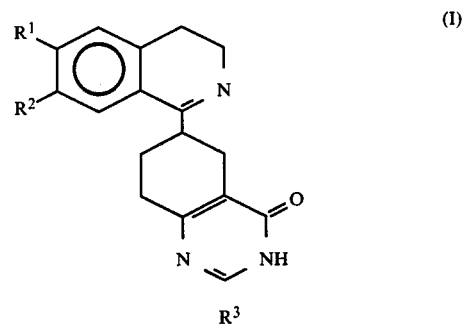

wherein
$R^1$ and $R^2$ each independently represents hdyroxyl or alkoxy having from 1 to 6 carbon atoms,
$R^3$ is alky having from 1 to 6 carbon atoms, optionally substituted phenyl, optionally substituted alkylphenyl having from 1 to 4 carbon atoms in the alkyl moiety or an optionally substiutted heterocyclic group, and acid addition and quaternary salts thereof.

Compounds of the formula (I) are pharmaceutically active, in particular show spasmolytic, analgesic, antipyretic activity and have a protecting effect in acute alcoholic intoxication.

9 Claims, No Drawings

1-(6-(2'-SUBSTIUTED-5', 6', 7', 8'-TETRAHYDRO-4',-OXO-QUINAZOLINO))-3-4-DIHYDRO-6,7-DISUBSTITUTED-ISOQUINOLINE DERIVATIVES AND PHARMACEUTICAL COMPOSTIONS CONTAINING THEM

The invention relates to new 1-[6-(2'-substituted-5',6',7',8'-tetrahydro-4'-oxo-quinazolino)]-3,4-dihydro-6,7-disubstituted-isoquinoline derivatives of the formula (I)

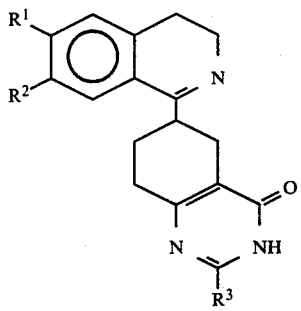

wherein
$R^1$ and $R^2$ each independently represents hydroxyl or alkoxy having from 1 to 6 carbon atoms,
$R^3$ is alkyl having from 1 to 6 carbon atoms, optionally substituted phenyl, optionally substituted alkylphenyl having from 1 to 4 carbon atoms in the alkyl moiety or an optionally substituted heterocyclic group,
and acid addition and quaternary salts thereof.

Compounds of the formula (I) are pharmaceutically active, in particular show spasmolytic, analgesic, antipyretic activity and have a protecting effect in acute alcoholic intoxication.

In the compounds of formula (I) the alkyl groups as such or as parts of other groups are straight-chained or branched saturated hydrocarbon groups having from 1 to 6 and 1 to 4 carbon atoms, respectively, e.g. methyl, ethyl, n-propyl, isopropyl, n-butyl, isobutyl, tert.-butyl, n-pentyl, isopentyl, n-hexyl or isohexyl groups, taking into account the restriction given for the number of carbon atoms.

$R^3$ as an alkylphenyl group having from 1 to 4 carbon atoms in the alkyl moiety preferably stands for benzyl.

The phenyl and benzyl groups may optionally be substituted by one or more, identical or different substitutents, preferably selected from the group consisting of halogen, e.g. fluorine, chlorine, bromine or iodine, preferably chlorine; alkoxy having from 1 to 6, preferably 1 to 4 carbon atoms, e.g. methoxy; alkyl having from 1 to 6, preferably 1 to 4 carbon atoms, e.g. methyl; and trifluoromethyl.

$R^3$ as a heterocyclic group represents a saturated or unsaturated carbocyclic group containing one or more identical or different heteroatoms. As a heteroatom for example nitrogen, oxygen or sulfur may be incorporated into the carbon chain, and the heterocyclic ring preferably is 5- or 6-membered. Particularly preferred are the saturated or unsaturated, 6-membered heterocyclic groups containing one or more nitrogen and/or oxygen atoms, e.g. pyridyl, 1,2,5,6-tetrahydro-pyridinyl, morpholinyl, piperazinyl, piperidinyl, pyrrolidinyl, etc. The heterocyclic groups may be substituted by one or more, identical or different substituents, e.g. by a further heterocyclic, e.g. piperidinyl group, $C_{1-4}$-alkyl, phenyl, hydroxyl or carbamoyl.

According to the invention compounds of the formula (I), wherein $R^1$, $R^2$ and $R^3$ are as defined above, and acid addition or quaternary salts are prepared by condensing an acid of the formula (II),

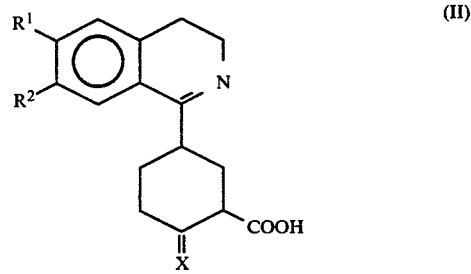

wherein
$R^1$ and $R^2$ are as defined above,
X is oxygen or an =NH group,
or a reactive derivative thereof, with a compound of the formula (III),

wherein $R^3$ is as defined above, or a salt thereof formed with an inorganic or organic acid, in an alkaline medium, and, if desired, converting a compound of the formula (I) obtained into an acid addition or quaternary salt thereof.

There are numerous pharmaceutically active isoquinoline derivatives known in the art (see e.g. Ehrhart-Ruschig, Arzneimittel, S. Ebel: Synthetische Arzneimittel; Verlag Chemie). Pharmaceutically active quinazolinone derivatives are known, too (Armarego, E. L. F.: Quinazolines-Fused Pyrimidines, Part I, Interscience Publishers, New York, 1967). There is not known, however, any publication which would disclose a combination of these two ring systems.

The keto-esters of the formula (II) used as starting materials in the process according to the invention, in which $R^1$, $R^2$ and X are as defined above, may be prepared according to our co-pending U.S. patent application Ser. No. 721,880, filed Apr. 10, 1985, now U.S. Pat. No. 4,622,329, for example from the corresponding diesters by ring closure. The diesters used in this procedure are either new compounds or can be prepared in a known manner, e.g. from the corresponding known diesters (which are unsubstituted in the 6,7-positions) or from the corresponding disubstituted 1-methyl-3,4-dihydroisoquinoline derivatives, which are known in the art.

As reactive derivatives of the compounds of formula (II) e.g. their esters or acid amides, preferably esters may be used.

Compounds of the formula (III), wherein $R^3$ is as defined above, are known and can be prepared by methods known in the organic chemistry, e.g. by reacting the corresponding iminoethers or salts thereof with ammonia.

The reaction of the acids of the formula (II) or reactive derivatives thereof with the compounds of the formula (III) or their salts formed with inorganic or organic acids proceeds in an alkaline medium smoothly already at room temperature, if desired, however, the reaction can be accelerated by increasing the temperature.

As alkaline catalysts for example alkali metal hydroxides, e.g. sodium or potassium hydroxide; alkali metal carbonates, e.g. sodium or potassium carbonate; alkali metal alcoholates, e.g. sodium or potassium alcoholate, can be used in the process according to the invention.

The reaction is carried out in an aqueous or organic medium. As organic solvent for example alcohols, e.g. methanol, ethanol; aromatic solvents, e.g. benzene; ethers, e.g. tetrahydrofurane, are employed.

In the compounds of formula (I) the substituents $R^1$ and/or $R^2$ and/or $R^3$ may be converted into other groups within the definition of $R^1$, $R^2$ and $R^3$, respectively. For example from the compounds, in which $R^1$ and/or $R^2$ is alkoxy having from 1 to 6 carbon atoms, the corresponding compounds containing hydroxyl groups as $R^1$ and/or $R^2$ can be prepared by desalkylation. Desalkylation can be performed in a known manner, e.g. by heating the alkoxy compound with hydrogen bromide or iodide, or by means of anhydrous aluminium chloride. On the other hand, the compounds of the formula (I), in which $R^1$ and/or $R^2$ stands for hydroxyl, can be converted into the corresponding alkoxy derivatives in a known manner. Methylation is preferably carried out with diazomethane or dimethyl sulfate, while the higher ethers can be prepared for example by the Williamson synthesis, using alkyl iodides.

Compounds of the formula (I) can be converted into their acid addition salts by reaction with suitable acids.

Salt formation can be carried out, for example, in an inert organic solvent, such as a $C_{1-6}$ aliphatic alcohol, by suspending or dissolving the compound of the formula (I) in the solvent and adding the selected acid or a solution thereof formed with the same solvent to the first solution until it becomes slightly acidic. Thereafter the acid addition salt separates and can be removed from the reaction mixture e.g. by filtration.

The compounds of the formula (I) or the salts thereof can be subjected, if desired, to further purification, e.g. recrystallization. The solvents used for recrystallization are selected depending on the solubility and crystallization properties of the compound to be crystallized.

The new compounds of the formula (I) and their physiologically acceptable acid addition salts can be formulated for therapeutic purposes. The invention therefore relates also to pharmaceutical compositions comprising as active ingredient at least one compound of formula (I) or a physiologically acceptable salt thereof, in association with pharmaceutical carriers and/or excipients. Carriers conventional for this purpose and suitable for parenteral or enteral administration as well as other additives may be used. As carriers solid or liquid compounds, for example water, gelatine, lactose, starch, pectin, magnesium stearate, stearic acid, talc, vegetable oils, such as peanut oil, olive oil, arabic gum, polyalkylene glycols, and Vaseline (registered Trade Mark) can be used. The compounds can be formulated as conventional pharmaceutical formulations, for example in a solid (globular and angular pills, dragées, capsules, e.g. hard gelatine capsules) or liquid (injectable oily or aqueous solutions or suspensions) form. The quantity of the solid carrier can be caried within wide ranges, but preferably is between 25 mg and 1 g. The compositions optionally contain also conventional pharmaceutical additives, such as preserving agents, wetting agents, salts for adjusting the osmotic pressure, buffers, flavouring and aroma substances.

The compositions according to the invention optionally contain the compounds of formula (I) in association with other known active ingredients. The unit doses are selected depending on the route of administration. The pharmaceutical compositions are prepared by conventional techniques including sieving, mixing, granulation, pressing or dissolution of the active ingredients. The formulations obtained are then subjected to additional conventional treatments, such as sterilization.

For the pharmacological tests CFLP (LATI) mice of both sexes, weighing 18 to 22 g each, and male Han. Wister (LATI) rats, weighing 160 to 180 g each, were used. The test materials were administered orally, in 30 mg/kg doses, in the form of a suspension containing 5% of Tween 80, one hour before the tests.

TEST METHODS

1. Metrazole spasm (MET), mice

After pretreatment, the animals were subcutaneously administered 125 mg/kg of pentylenetetrazole. The animals which did not show a tonic extensoric spasm and survived the experiment were regarded protected. Observation time: one hour [Everett, L. M. and Richards, R. K.: J. Pharmacol. Exp. Ther. 81, 402 (1944)].

2. Strychnine spasm (STRY), mice

One hour after pretreatment the animals were intraperitoneally administered 2.5 mg/kg of strychnine nitrate to induce tonic extensoric spasm. The animals which showed no sign of spasm after treatment were considered protected [Kerley, T. L. et al.: J. Pharmacol. Exp. Ther. 132, 360 (1961)].

3. Analgesic activity (ANAL), mice

One hour after pretreatment, mice were administered 0.3 ml of a 0.6% acetic acid solution intraperitoneally, as a pain stimulus. The frequency of writhing syndrom was registered for 30 minutes. The changes observed as a result of treatment with the test compounds are related to the mean value of the frequency of writhing syndrom in the control group, and the difference is expressed in percentage [Koster, R. et al.: J. Pharmacol. Exp. Ther. 72, 74 (1941)].

4. Antipyretic activity (PYR), mice

On rats hyperthermia was induced by a brewer's yeast suspension (0.5% of brewer's yeast, 1% of arabic gum made up to 0.3 ml with water) administered subcutaneously. After 4 hours, the animals were treated with the test materials, and the tracheal temperature was registered with an ELAB thermometer (Type TE-3) every hour, altogether for 4 hours. The antipyretic activity is expressed in percentage of the animals which had a 1° C. lower temperature after treatment than the mean temperature of the control group, treated with solvent alone [Nimegeers, C. J. E. et al.: Arzneim. Forsch. 25, 1591 (1975)].

5. Acute alcoholic intoxication (ETA), rats

One hour after pretreatment the animals were intraperitoneally administered 3.5 g/kg of ethyl alcohol. The narcosis time was registered and the mean times of the individual test groups were related to the narcosis time of the control group. The difference is expressed in percentage.

The results of pharmacological tests are set forth in Table I below.

Test compounds:

Compound "A": 1-[6'-(2'-piperidino-5',6',7',8'-tetrahydro-4'-oxo-quinazolinyl)]-3,4-dihydro-6,7-dimethoxy-isoquinoline;

Compound "B": 1-{6'-[2'-(4"-p-chlorophenyl-piperidino-4"-ol)-5',6',7',8'-tetrahydro-4'-oxo-quinazolinyl]}-3,4-dihydro-6,7-dimethoxy-isoquinoline;

Compound "C": 1-[6'-(2'-piperidino-4"-carboxamide)-5',6',7',8'-tetrahydro-4'-oxo-quinazolinyl]-3,4-dihydro-6,7-dimethoxy-isoquinoline;

Compound "D": 1-{6'-[2'-(3",4",5"-trimethoxyphenyl)-5',6',7',8'-tetrahydro-4'-oxo-quinazolinyl]}-3,4-dihydro-6,7-dimethoxy-isoquinoline;

Compound "E": 1-{6'-[2'-(1",2",5",6"-tetrahydro-4"-phenyl-pyridino)-5',6',7',8'-tetrahydro-4'-oxo-quinazolinyl]}-3,4-dihydro-6,7-dimethoxy-isoquinoline Compound "F": 1-{6'-[2'-N-(2"-chlorophenyl)-piperizino-5',6',7'8'-tetrahydro-4'-oxo-quinazolinyl]}-3,4-dihydro-6,7-dimethoxy-isoquinoline;

Compound "G": 1-{6'-[2'-(3"-methyl)-phenyl-5',6',7',8'-tetrahydro-4'-oxo-quinazolinyl]}-3,4-dihydro-6,7-dimethoxy-isoquinoline;

Compound "H": 1-{6'-[2'-(3"-pyridine)-5',6',7',8'-tetrahydro-4'-oxo-quinazolinyl]}-3,4-dihydro-6,7-dimethoxy-isoquinoline;

Compound "I": 1-[6'-(2'-pyrrolidino-5',6',7',8'-tetrahydro-4'-oxo-quinazolinyl)]-3,4-dihydro-6,7-dimethoxy-isoquinoline

TABLE I

| Compound | Anticonvulsive activity (%) | | | | |
|---|---|---|---|---|---|
| | MET | STRY | ANAL | PYR | ETA |
| "A" | | | −40 | | |
| "B" | | | | −40% | −45% |
| "C" | | | | | −58% |
| "D" | 40 | | | | |
| "E" | | 40 | | | |
| "F" | 40 | | | | |
| "G" | ED$_{50}$ = 21.2 mg/kg | | | | |
| "H" | | | | | −40% |
| "I" | 40 | 40 | ED$_{50}$ = | −40% | |

TABLE I-continued

| Compound | Anticonvulsive activity (%) | | | | |
|---|---|---|---|---|---|
| | MET | STRY | ANAL | PYR | ETA |
| | | | 19.3 mg/kg | | |

The results show that especially compound "G" shows a remarkable anticonvulsive activity, having an ED$_{50}$-value of 21.2 mg/kg. As to the analgesic activity of the test compounds, Compound "I" is the most effective, with an ED$_{50}$-value of 19.3 mg/kg. Compounds "B" and "I" show a substantial antipyretic activity, while compounds "B", "C" and "H" have a remarkable protecting effect in acute alcoholic intoxication.

The invention is elucidated in more detail by the aid of the following non-limiting Examples.

EXAMPLE 1

1-[6'-(2'-Phenyl-5',6',7',8'-tetrahydro-4'-oxoquinazolinyl)]-3,4-dihydro-6,7-dimethoxy-isoquinoline 16.7 g (0.05 mole) of 1-[(3'-methoxycarbonyl-4'-oxo)-1-cyclohexyl]-3,4-dihydro-6,7-dimethoxy-isoquinoline and 8.6 g (0.055 mole) of benzamidine hydrochloride are suspended in 200 ml of dry ethyl alcohol, and a solution of 1.26 g (0.055 g-atom) of sodium metal in 50 ml of dry ethanol is added. The reaction mixture is refluxed under stirring for 6 hours, and the solvent is distilled off. The residue is suspensed in 100 ml of water, separated by filtration in vacuo, washed with water and subsequently acetone, and dried. The product is crystallized from toluene.

The physical and analytical data of the product obtained and of the 2'-substituted derivatives prepared from 1-[(3'-methoxy- or -ethoxy-carbonyl-4'-oxo)-1-cyclohexyl]-3,4-dihydro-6,7-dimethoxy- or -diethoxy-isoquinoline in an analogous way are set forth in Table II.

The hydrochlorides of the compounds are prepared by suspending the bases in aqueous alcohol, adding a one and a half-fold volume of aqueous hydrochloric acid solution, evaporating the solution obtained, triturating the residue with anhydrous or 96% ethanol, filtering and finally recrystallizing the product obtained.

TABLE II

| No. of compound | R$^1$ = R$^2$ | R$^3$ | RX | Compounds of formula (I) Formula/molecular weight | Mp. (°C.) Solvent | Analysis | | Yield (%) |
|---|---|---|---|---|---|---|---|---|
| | | | | | | Calc. (%) | Found (%) | |
| 1 | —OCH$_3$ | —C$_6$H$_5$ | — | C$_{25}$H$_{27}$O$_3$N$_3$ 417.51 | 248 toluene | C 71.92 H 6.51 N 10.0 | 72.13 6.38 9.98 | 66 |
| 2 | —OCH$_3$ | —C$_6$H$_5$ | HCl | C$_{25}$H$_{28}$O$_3$N$_3$Cl 453.98 | 275–76 90% ethanol | C 66.43 H 5.79 N 9.29 | 66.22 6.08 9.12 | |
| 3 | —OCH$_3$ | —C$_6$H$_4$Cl(m) | — | C$_{25}$H$_{24}$N$_3$O$_3$Cl 449.94 | 154–155 DMF | C 66.73 H 5.57 N 9.33 | 66.30 5.68 9.07 | 72 |
| 4 | —OCH$_3$ | —C$_6$H$_4$Cl(m) | HCl | C$_{25}$H$_{25}$N$_3$O$_3$Cl$_2$ 486.40 | 288–289 96% ethanol | C 61.73 H 5.18 N 8.63 | 62.02 5.35 8.51 | |
| 5 | —OCH$_3$ | —C$_6$H$_3$(OCH$_3$)$_2$(m,p) | — | C$_{27}$H$_{29}$N$_3$O$_5$ 475.54 | 275 toluene | C 68.19 H 6.14 N 8.89 | 67.86 6.25 8.88 | 70 |
| 6 | —OCH$_3$ | —C$_6$H$_3$(OCH$_3$)$_2$(m,p) | HCl | C$_{27}$H$_{30}$N$_3$O$_5$Cl 512.01 | 252–53 96% ethanol | C 63.37 .H 5.40 N 8.20 | 63.70 6.12 8.35 | |
| 7 | —OCH$_3$ | —CH$_3$ | — | C$_{20}$H$_{23}$N$_3$O$_3$ 353.42 | 260–261 96% ethanol | C 67.97 H 6.55 N 11.88 | 67.85 6.72 11.56 | 52 |
| 8 | —OCH$_3$ | —CH$_3$ | 2HCl | C$_{20}$H$_{25}$N$_3$O$_3$Cl$_2$ 426.34 | 268–269 96% ethanol- | C 56.34 H 5.91 | 56.58 6.16 | |

TABLE II-continued

Compounds of formula (I)

| No. of compound | $R^1 = R^2$ | $R^3$ | RX | Formula/molecular weight | Mp. (°C.) Solvent | | Analysis Calc. (%) | Found (%) | Yield (%) |
|---|---|---|---|---|---|---|---|---|---|
| 9 | —OCH$_3$ | —CH$_2$C$_6$H$_4$Cl(p) | — | C$_{26}$H$_{26}$N$_3$O$_3$Cl 463.96 | 286–287 ether DMF | N C H N | 9.85 67.30 5.64 9.05 | 10.2 67.56 5.90 9.09 | 78 |
| 10 | —OCH$_3$ | —CH$_2$C$_6$H$_4$Cl(p) | 2HCl | C$_{26}$H$_{28}$N$_3$O$_3$Cl$_3$ 536.89 | 249–250 96% ethanol-ether | C H N | 58.16 5.69 7.82 | 58.18 5.35 7.47 | |
| 11 | —OCH$_3$ | pyrid-4-yl | — | C$_{24}$H$_{24}$N$_4$O$_3$ 416.58 | 258–259 toluene | C H N | 69.21 5.80 13.45 | 68.86 6.17 13.28 | 54 |
| 12 | —OCH$_3$ | pyrid-4-yl | 2HCl | C$_{24}$H$_{26}$N$_4$O$_3$Cl$_2$ 489.40 | 265–266 96% ethanol-ether | C H N | 58.90 5.35 11.44 | 58.73 5.75 11.80 | |
| 13 | —OC$_2$H$_5$ | —C$_6$H$_4$Cl(m) | — | C$_{27}$H$_{28}$N$_3$O$_3$Cl 477.99 | 198 ethanol (decomp.) | C H N | 67.84 5.90 8.79 | 68.22 6.19 8.37 | 55 |
| 14 | —OC$_2$H$_5$ | —C$_6$H$_4$Cl(m) | HCl | C$_{27}$H$_{29}$N$_3$O$_3$Cl$_2$ 514.45 | ethanol | C H N Cl | 63.03 5.68 8.16 13.78 | 62.28 6.04 7.59 14.04 | |
| 15 | —OC$_2$H$_5$ | —CH$_3$ | — | C$_{22}$H$_{27}$N$_3$O$_3$ 381.47 | 225 ethanol (decomp.) | C H N | 69.26 7.13 11.01 | 68.57 7.15 10.80 | 48 |
| 16 | —OC$_2$H$_5$ | —CH$_3$ | HBr | C$_{22}$H$_{28}$N$_3$O$_3$Br 462.39 | 225 ethanol (decomp.) | C H N | 57.14 6.10 9.08 | 56.77 6.24 8.97 | |
| 17 | —OC$_2$H$_5$ | —CH$_2$C$_6$H$_4$Cl(p) | — | C$_{28}$H$_{30}$N$_3$O$_3$Cl 492.02 | 250 DMF (decomp.) | C H N | 68.35 6.14 8.54 | 68.35 6.83 8.56 | 58 |
| 18 | —OC$_2$H$_5$ | —CH$_2$C$_6$H$_4$Cl(p) | HBr | C$_{28}$H$_{31}$N$_3$O$_3$BrCl 572.93 | 261 ethanol (decomp.) | C H N | 58.69 5.45 7.33 | 58.34 5.65 7.12 | |

EXAMPLE 2

1-[(6'-(2'-Piperidino-5',6',7',8'-tetrahydro-4'-oxo-quinazolinyl)]-3,4-dihydro-6,7-dimethoxy-isoquinoline 16.7 g (0.05 mole) of 1-[(3'-methoxycarbonyl-4'-oxo)-1-cyclohexyl]-3,4-dihydro-6,7-dimethoxy-isoquinoline and 9.69 g (0.0275 mole) of piperidinoguanidine sulfate are suspended in 200 ml of dry ethanol, and the solution of 1.26 g (0.055 g-atom) of sodium metal in 50 ml of dry ethanol is added to the suspension. The reaction mixture is refluxed under stirring for 6 hours, and the solvent is distilled off. The residue is suspended in 100 ml of water, filtered under vacuum, washed with water and acetone and dried. The aimed product obtained is purified by crystallization from toluene or ethanol.

The physical and analytical data of the product obtained and of the corresponding 2'-substituted derivatives prepared from 1-[(3'-methoxy- or -ethoxycarbonyl-4'-oxo)-1-cyclohexyl]-3,4-dihydro-6,7-dimethoxy- or -diethoxyisoquinoline are set forth in Table III.

The hydrochlorides of the compounds obtained are prepared as described in Example 1.

TABLE III

Compounds of formula (I)

| No. of compound | $R^1 = R^2$ | $R^3$ | HX | Formula/molecular weight | Mp. (°C.) Solvent | | Analysis Calc. (%) | Found (%) | Yield (%) |
|---|---|---|---|---|---|---|---|---|---|
| 19 | —OCH$_3$ | piperidino | — | C$_{24}$H$_{30}$N$_4$O$_3$ 422.53 | 278–79 ethanol | C H N | 68.22 7.15 13.25 | 68.33 7.37 13.48 | 64 |
| 20 | —OCH$_3$ | piperidino | 2HCl | C$_{24}$H$_{32}$N$_4$O$_3$Cl$_2$ 495.44 | 248–250 ethanol-ether (decomp.) | C H N Cl | 58.18 6.51 11.30 14.31 | 57.86 6.29 10.95 14.66 | |
| 21 | —OCH$_3$ | morpholin-4-yl | — | C$_{23}$H$_{28}$N$_4$O$_4$ 424.50 | 286 ethanol (decomp.) | C H N | 65.07 6.64 13.19 | 65.45 6.52 13.49 | 52 |
| 22 | —OCH$_3$ | morpholin-4-yl | 2HCl | C$_{23}$H$_{30}$N$_4$O$_4$Cl$_2$ 497.42 | 234–235 ethanol-ether (decomp.) | C H N Cl | 55.55 6.08 11.26 14.22 | 55.24 6.41 10.95 14.60 | |
| 23 | —OCH$_3$ | 1-methyl-piperazin-4-yl | 3HCl | C$_{24}$H$_{31}$N$_5$O$_3$ 437.54 | 241 ethanol | C H N | 65.88 7.14 16.00 | 66.17 7.50 15.72 | 58 |
| 24 | —OCH$_3$ | 1-methyl-piperazin-4-yl | 3HCl | C$_{24}$H$_{34}$N$_5$O$_3$Cl$_3$ 546.92 | 258–260 (decomp.) ethanol-ether | C H N Cl | 52.70 6.26 12.80 19.44 | 52.31 6.54 12.40 19.10 | |
| 25 | —OCH$_3$ | 1-phenyl-piperazin-4-yl | — | C$_{29}$H$_{33}$N$_5$O$_3$ 499.62 | 241–242 DMF | C H N | 69.71 6.65 14.01 | 70.08 6.82 13.89 | 65 |

TABLE III-continued

Compounds of formula (I)

| No. of compound | $R^1 = R^2$ | $R^3$ | HX | Formula/molecular weight | Mp. (°C.) Solvent | Analysis Calc. (%) | Found (%) | Yield (%) |
|---|---|---|---|---|---|---|---|---|
| 26 | —OCH$_3$ | 1-phenyl-piperazin-4-yl | 3HCl | C$_{29}$H$_{36}$N$_5$O$_3$Cl$_3$ 609.00 | 232–234 ethanol | C 57.19<br>H 5.95<br>N 11.49 | 56.85<br>6.30<br>11.98 | |
| 27 | —OCH$_3$ | 4-piperidino-4-carbamoyl-piperidin-1-yl | 3HCl | C$_{30}$H$_{43}$N$_6$O$_4$Cl$_3$ 658.07 | 243–245 (decom.) ethanol | C 54.75<br>H 6.58<br>N 12.77<br>Cl 16.16 | 54.43<br>6.97<br>12.80<br>15.82 | 47 |
| 28 | —OCH$_3$ | 4-phenyl-4-hydroxy-piperidin-1-yl | — | C$_{30}$H$_{34}$N$_4$O$_4$Cl 550.08 | 160–162 DMF | C 65.50<br>H 6.23<br>N 10.18 | 65.87<br>6.55<br>9.88 | 61 |
| 29 | —OCH$_3$ | 4-phenyl-4-hydroxy-piperidin-1-yl | 2HCl | C$_{30}$H$_{36}$N$_4$O$_4$Cl$_3$ 623.60 | over 350° C. (decomp. from 270) water | C 57.83<br>H 5.92<br>N 8.99<br>Cl 17.07 | 57.45<br>6.13<br>8.63<br>17.40 | |
| 30 | —OCH$_3$ | 4-phenyl-1,2,5,6-tetrahydro-pyridin-1-yl | — | C$_{30}$H$_{32}$O$_3$N$_4$ 496.61 | 217–218 toluene | C 72.55<br>H 6.49<br>N 11.28 | 72.82<br>6.70<br>11.44 | 64 |
| 31 | —OCH$_3$ | 4-phenyl-1,2,5,6-tetrahydro-pyridin-1-yl | 2HCl | C$_{30}$H$_{34}$O$_3$N$_4$Cl$_2$ 569.53 | 250–255 (decomp.) 96% ethanol | C 63.26<br>H 6.01<br>N 9.83 | 63.28<br>6.37<br>9.80 | |
| 32 | —OCH$_3$ | 2-trifluor-methyl-benzyl | — | C$_{27}$H$_{26}$N$_3$O$_3$F$_3$ 497.52 | 269–270 DMF | C 67.52<br>H 7.33<br>N 9.26 | 68.49<br>7.41<br>10.11 | 57 |
| 33 | —OCH$_3$ | pyrrolidino | — | C$_{23}$H$_{28}$N$_4$O$_3$ 408.50 | 274–275 ethanol | C 67.67<br>H 6.9<br>N 13.71 | 67.85<br>7.2<br>13.55 | 62 |
| 34 | —OCH$_3$ | pyrid-3-yl | — | C$_{24}$H$_{24}$N$_4$O$_3$ 416.48 | 221–222 ethanol | C 69.21<br>H 5.80<br>N 13.45 | 69.41<br>6.12<br>13.22 | 56 |
| 35 | —OCH$_3$ | 3-methyl-phenyl | — | C$_{26}$H$_{27}$N$_3$O$_3$ 429.52 | 234–235 | C 72.70<br>H 6.33<br>N 9.78 | 73.11<br>6.68<br>10.05 | 58 |
| 36 | —OCH$_3$ | 2-Cl—phenyl-piperazine | — | C$_{29}$H$_{32}$N$_5$O$_3$Cl 534.06 | 254 (decomp.) DMF | C 65.22<br>H 6.03<br>N 13.11 | 64.95<br>6.27<br>13.03 | 57 |
| 37 | —OCH$_3$ | 3,4,5-tri-methoxy-phenyl | 2HCl | C$_{28}$H$_{33}$N$_3$O$_6$Cl$_2$ 578.49 | 218–220 ethanol-ether | C 62.04<br>H 5.95<br>N 12.25 | 61.70<br>5.74<br>11.96 | 61 |
| 38 | —OCH$_3$ | N—methyl-piperazino | 3HCl | C$_{24}$H$_{34}$N$_5$O$_3$Cl$_3$ 546.92 | 258–260 (decomp.) ethanol-ether | C 52.70<br>H 6.26<br>N 12.80<br>Cl 19.44 | 52.31<br>6.54<br>12.40<br>19.10 | 53 |
| 39 | CH$_3$O— | 4-(4'-Cl—phenyl)-4-OH— | 2HCl | C$_{30}$H$_{36}$N$_4$O$_4$Cl$_3$ 623.00 | from 270 (decomp.) ethanol-ether | C 57.83<br>H 5.82<br>N 8.99<br>Cl 17.07 | 57.45<br>6.11<br>8.63<br>17.40 | 51 |
| 40 | CH$_3$O— | piperidino | 2HCl | C$_{24}$H$_{32}$N$_4$O$_3$Cl$_2$ 495.44 | 248–250 (decomp.) ethanol-ether | C 58.98<br>H 6.51<br>N 11.30 | 57.86<br>6.29<br>10.95 | 56 |

EXAMPLE 3

1-[6'-(2'-Phenyl-5',6',7',8'-tetrahydro-4'-oxo-quinazolinyl)]-3,4-dihydro-6,7-dihydroxy-isoquinoline hydrobromide 8.34 g (0.02 mole) of 1-[6'-(2'-phenyl-5',6',7',8'-tetrahydro-4'-oxo-quinazolinyl)]-3,4-dihydro-6,7-dimethoxy-isoquinoline are suspended in 40 ml of a 40% aqueous hydrogen bromide solution, and the suspension is slightly boiled on an oil bath for one hour.

As the reaction proceeds upon boiling the starting compound is slowly dissolved. The progress of the reaction is monitored by thin-layer chromatography. When the reaction is complete, the mixture is evaporated to dryness in vacuo, and the product is crystallized from aqueous ethanol.

Yield: 78%.

Melting point: 293° to 295° C.

Analysis for C$_{23}$H$_{23}$N$_3$O$_3$Br (549.26): calculated: C 50.29%, H 4.22%, N 7.65%; found: C 50.61%, H 4.55%, N 7.29%.

We claim:

1. A 1-[6-(2'-substituted-5',6',7',8'-tetrahydro-4'-oxo-quinazoline)]-3,4-dihydro-6,7-disubstituted-isoquinoline derivative of the formula (I)

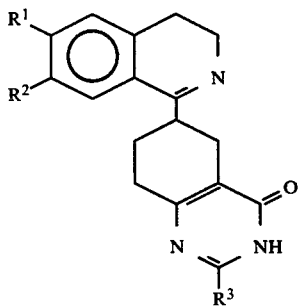

wherein
R¹ and R² each independently represents hydroxyl or alkoxy having from 1 to 6 carbon atoms, R³ is alkyl having from 1 to 6 carbon atoms, unsubstituted phenyl or phenyl substituted by halogen, alkoxy of 1–6 carbons, alkyl of 1–6 carbons or trifluoromethyl, unsubstituted alkylphenyl having from 1 to 4 carbon atoms in the alkyl moiety or said alkylphenyl substituted by halogen, alkoxy of 1–6 carbons, alkyl of 1–6 carbons or trifluoromethyl, or a 5- or 6-membered heterocyclic ring having one or two oxygen, nitrogen or sulfur atoms, said heterocyclic ring being unsubstituted or substituted by a $C_1$–$C_4$-alkyl, phenyl, hydroxyl, carbamyl or piperidinyl group, and physiologically acceptable acid addition and quaternary salts thereof.

2. A compound of the formula (I) of claim 1, in which R¹ and R² are both methoxy or ethoxy, while R³ is as defined in claim 1.

3. A compound selected from the group consisting of
1-[6'-(2'-piperidino-5',6',7',8'-tetrahydro-4'-oxo-quinazolinyl)]-3,4-dihydro-6,7-dimethoxy-isoquinoline;

1-{6'-[2'-(4″-p-chlorophenyl-piperidino-4″-ol)-5',6',7',8'-tetrahydro-4'-oxo-quinazolinyl]}-3,4-dihydro-6,7-dimethoxy-isoquinoline;

1-[6'-(2'-piperidino-4″-carboxamide)-5',6',7',8'-tetrahydro-4'-oxo-quinazolinyl]-3,4-dihydro-6,7-dimethoxy-isoquinoline;

1-{6'-[2'-(3″,4″,5″-trimethoxyphenyl)-5',6',7',8'-tetrahydro-4'-oxo-quinazolinyl]}-3,4-dihydro-6,7-dimethoxy-isoquinoline;

1-{6'-[2'-(1″,2″,5″,6″-tetrahydro-4″-phenyl-pyridino)-5',6',7',8'-tetrahydro-4'-oxo-quinazolinyl]}-3,4-dihydro-6,7-dimethoxy-isoquinoline;

1-{6'-[2'-N-(2″-chlorophenyl)-piperazino-5',6',7',8'-tetrahydro-4'-oxo-quinazolinyl]}-3,4-dihydro-6,7-dimethoxy-isoquinoline;

1-{6'-[2'-(3″-dimethyl)-phenyl-5',6',7',8'-tetrahydro-4'-oxo-quinazolinyl]}-3,4-dihydro-6,7-dimethoxy-isoquinoline;

1-{6'-[2'-(3″-pyridine)-5',6',7',8'-tetrahydro-4'-oxo-quinazolinyl]}-3,4-dihydro-6,7-dimethoxy-isoquinoline;

1-[6'-(2'-pyrrolidino-5',6',7',8'-tetrahydro-4'-oxo-quinazolinyl)]-3,4-dihydro-6,7-dimethoxy-isoquinoline.

4. The compound of claim 3 which is 1-[6'-(2'-piperidino-5',6',7',8'-tetrahydro-4'-oxoquinazolinyl)]-3,4-dihydro-6,7-dimethoxy-isoquinoline.

5. The compound of claim 3 which is 1-{6'-[2'-(4″-p-chlorophenyl-piperidino-4″-ol)-5',6',7',8'-tetrahydro-4'-oxo-quinazolinyl}-3,4-dihydro-6,7-dimethoxy-isoquinoline.

6. The compound of claim 3 which is 1-[6'-(2'-piperidino-4″-carboxamide)-5',6',7',8'-tetrahydro-4'-oxo-quinazolinyl]-3,4-dihydro-6,7-dimethoxy-isoquinoline.

7. The compound of claim 3 which is 1-{6'-[2'-(3″-pyridine)-5',6',7',8'-tetrahydro-4'-oxo-quinazolinyl}-3,4-dihydro-6,7-dimethoxy-isoquinoline.

8. The compound of claim 3 which is 1-[6'-(2'-pyrrolidino-5',6',7',8'-tetrahydro-4'-oxo-quinazolinyl)]-3,4dihydro-6,7-dimethoxy-isoquinoline.

9. A pharmaceutical composition having spasmolytic, analgesic, anti-pyretic and/or acute alcoholic intoxication protecting activity comprising as an active ingredient an effective amount of at least one compound of formula (I) of claim 1 or physiologically acceptable salts thereof, in association with pharmaceutical carriers and/or excipients.

* * * * *

UNITED STATES PATENT AND TRADEMARK OFFICE
CERTIFICATE OF CORRECTION

PATENT NO. : 4,677,109

DATED : June 30, 1987

INVENTOR(S) : Gabor BERNATH et al.

It is certified that error appears in the above-identified patent and that said Letters Patent is hereby corrected as shown below:

In the Abstract:

$R^3$ is [alky] having . . - should be:

$R^3$ is alkyl having . . .

Column 12, line 39

[3,4 dihydro-6,7-] should be:

3,4-dihydro-6,7-

Signed and Sealed this

First Day of December, 1987

Attest:

DONALD J. QUIGG

Attesting Officer     Commissioner of Patents and Trademarks